(12) United States Patent
Astle

(10) Patent No.: US 6,537,752 B1
(45) Date of Patent: Mar. 25, 2003

(54) TEMPERATURE CONTROL SYSTEM FOR POLYMERASE CHAIN REACTION

(76) Inventor: Thomas W. Astle, 607 Harborview Rd., Orange, CT (US) 06477

( * ) Notice: Subject to any disclaimer, the term of this patent is extended or adjusted under 35 U.S.C. 154(b) by 0 days.

(21) Appl. No.: 09/425,070

(22) Filed: Mar. 22, 1999

Related U.S. Application Data

(63) Continuation-in-part of application No. 09/198,018, filed on Nov. 23, 1998.
(60) Provisional application No. 60/067,895, filed on Dec. 8, 1997, provisional application No. 60/073,329, filed on Feb. 2, 1998, and provisional application No. 60/095,497, filed on Aug. 6, 1998.

(51) Int. Cl.⁷ .............................. C12M 1/40; C12M 1/38
(52) U.S. Cl. .............................. 435/6; 436/43; 436/180; 422/63; 422/66; 422/81; 422/99; 422/100; 422/103; 422/131; 435/91.2; 435/285.1; 435/288.4; 435/303.1
(58) Field of Search .............................. 422/63, 81, 66, 422/99, 100, 103, 131; 436/43, 180; 435/6, 91.2, 303.1, 288.4, 285.1; 219/428–430, 433

(56) References Cited

U.S. PATENT DOCUMENTS

| | | | | |
|---|---|---|---|---|
| 4,883,642 A | * | 11/1989 | Bisconte | 422/66 |
| 5,123,477 A | * | 6/1992 | Tyler | 165/2 |
| 5,187,084 A | * | 2/1993 | Hallsby | 435/91 |
| 5,302,347 A | * | 4/1994 | Van Den Berg et al. | 422/67 |
| 5,504,007 A | * | 4/1996 | Haynes | 435/285.1 |
| 5,508,197 A | * | 4/1996 | Hansen et al. | 435/285.1 |
| 5,720,923 A | * | 2/1998 | Haff et al. | 422/68.1 |

* cited by examiner

*Primary Examiner*—Jill Warden
*Assistant Examiner*—Kathryn Bex
(74) *Attorney, Agent, or Firm*—John H. Crozier

(57) ABSTRACT

In a preferred embodiment, a polymerase chain reaction temperature control system, including: a first tank into which a multiwell sample carrier may be placed; apparatus to introduce first temperature controlled heat transfer medium into the first tank for a first predetermined length of time; and apparatus to subsequently introduce at least a second second temperature controlled heat transfer medium into the first tank for at least a second predetermined length of time.

10 Claims, 2 Drawing Sheets

TEMPERATURE CONTROL SYSTEM FOR POLYMERASE CHAIN REACTION

CROSS-REFERENCE TO RELATED APPLICATION

The present application is a continuation-in-part of copending application Ser. No. 09/198,018, filed Nov. 23, 1998, and titled ULTRA HIGH THROUGHPUT BIOASSAY SCREENING SYSTEM, which application claims the benefit of filing dates of Provisional Patent Applications Nos. 60/067,895, filed Dec. 8, 1997, and titled ULTRA HIGH THROUGHPUT BIOASSAY SCREENING SYSTEM AND METHOD; Ser. No. 60/073,329, filed Feb. 2, 1998, and titled ULTRAHIGH THROUGHPUT BIOASSAY SYSTEM AND METHOD; and Ser. No. 60/095,497, filed Aug. 6, 1998, and titled USE OF CONTINUOUS CARRIER TAPE FOR POLYMERASE CHAIN REACTIONS, the disclosures of which applications are incorporated by reference hereinto.

BACKGROUND OF THE INVENTION

1. Field of the Invention

The present invention relates to temperature control systems for polymerase chain reactions generally and, more particularly, but not by way of limitation, to a novel temperature control system for polymerase chain reactions that is simple and affords an improved degree of control.

2. Background Art

Polymerase chain reaction (PCR) is a technique that is commonly used in genomic studies and other areas of biotechnology. It consists of taking biological samples through different temperature cycles multiple times to amplify the DNA. Typically, three different temperatures are used: $T_1$, $T_2$, and $T_3$. The sample or samples are cycled through the three temperatures in a set sequence of times for each specific reaction protocol.

A typical protocol might be as follows: Hold the samples at 95 degrees Centigrade for five minutes to start the sequence. Then, sequentially, hold the sample(s) at 95 degrees Centigrade for 15 seconds, hold the samples(s) at 55 degrees Centigrade for 15 seconds, and hold the sample(s) at 72 degrees Centigrade for 30 seconds. This one-minute cycle is repeated 10 times. Then, sequentially, the samples are held at 89 degrees Centigrade for 15 seconds, held at 55 degrees Centigrade for 15 seconds, and held at 72 degrees Centigrade for 30 seconds. The second temperature sequence is repeated 20 times. The samples are then held at 72 degrees Centigrade for 10 minutes as a final step. The samples may then be held at four degrees Centigrade for a longer period of time until used.

The conventional method of conducting such protocols is to place multiple DNA samples in a 96-or 384-well microplate and then the plate is robotically switched between liquid baths, held at predetermined temperatures, for the indicated periods of time. In addition to being relatively expensive, such method suffers from not being able to control the ramp rate of temperature change.

Accordingly, it is a principal object of the present invention to provide a system for conducting PCR studies that is simple and economical.

It is an additional object of the invention to provide such a system that permits for accurate temperature control of the heat transfer medium in the system.

It is a further object of the invention to provide such a system that provides control of the ramp rate of temperature change between steps in the reaction protocol.

Other objects of the present invention, as well as particular features, elements, and advantages thereof, will be elucidated in, or be apparent from, the following description and the accompanying drawing figures.

SUMMARY OF THE INVENTION

The present invention achieves the above objects, among others, by providing, in a preferred embodiment, a polymerase chain reaction temperature control system, comprising: a first tank into which a multiwell sample carrier may be placed; means to introduce first temperature controlled heat transfer medium into said first tank for a first predetermined length of time; and means to subsequently introduce at least a second second temperature controlled heat transfer medium into said first tank for at least a second predetermined length of time.

BRIEF DESCRIPTION OF THE DRAWING

Understanding of the present invention and the various aspects thereof will be facilitated by reference to the accompanying drawing figure, submitted for purposes of illustration only and not intended to define the scope of the invention, on which.

DETAILED DESCRIPTION OF THE PREFERRED EMBODIMENTS

The above-referenced patent applications describe the use of a carrier tape for use in bioassays. The carrier tape has a large number of wells formed therein into which wells various materials may be introduced for reaction and/or incubation. The wells may be sealed with a sealing member and then the carrier tape is formed into a roll. A roll of such carrier tape four inches wide by 16 inches in diameter will hold approximately 100,000 discrete samples. The applications describe the tape and the methods of filing, sealing, and handling the tape.

Such a sealed carrier tape is especially useful in practicing the present invention. However, suitably sealed conventional microplates having 96 or 384 or any other number of wells may be employed in the invention as well.

Figure 2:
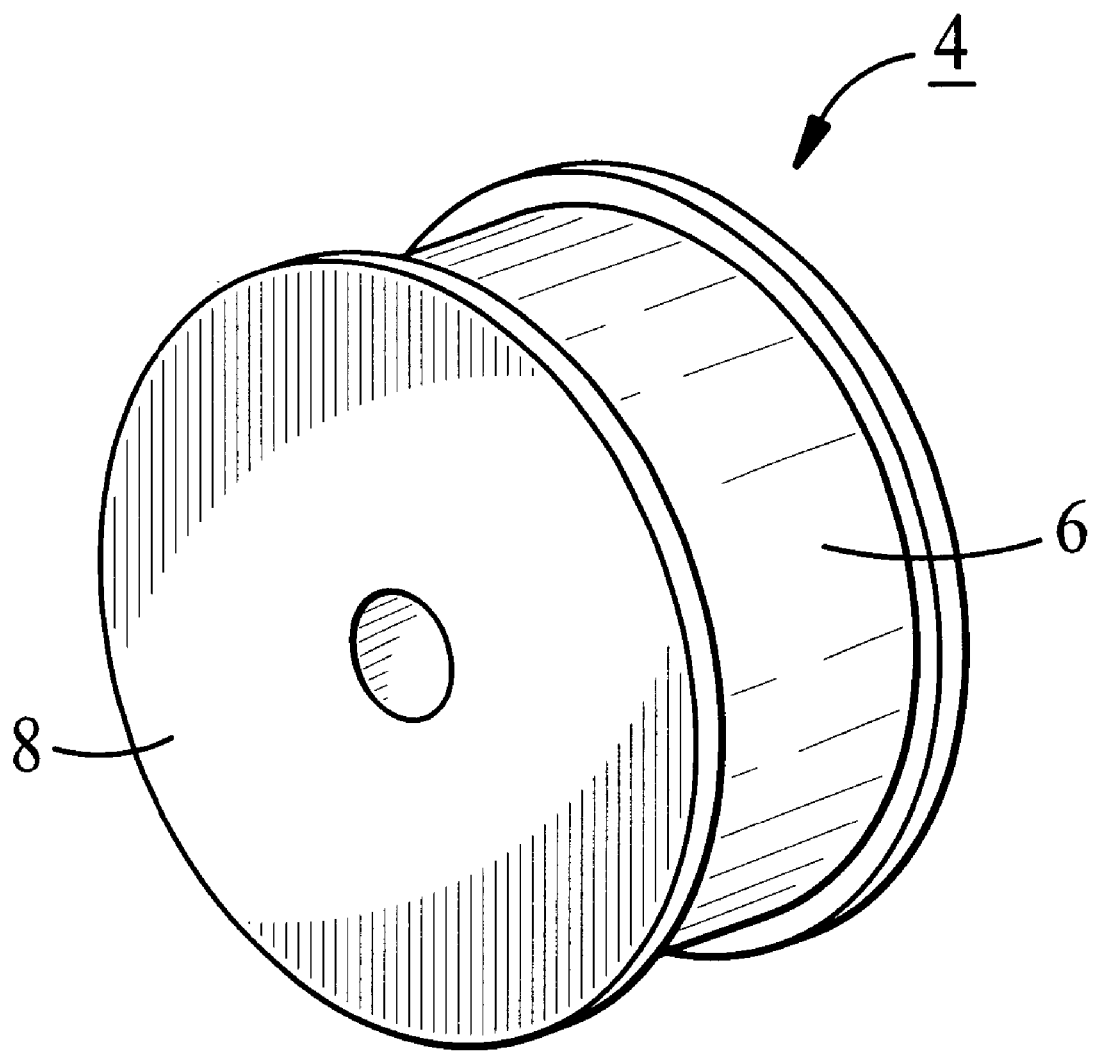
FIG. 2 is an isometric view of a roll of carrier tape useful in practicing the present invention.

FIG. 2 illustrates a suitable roll of such carrier tape, the roll being generally indicated by the reference numeral 4. Roll 4 includes a plurality of patterns of wells, as at 6, and may be wound on a reel 8.

Figure 1:
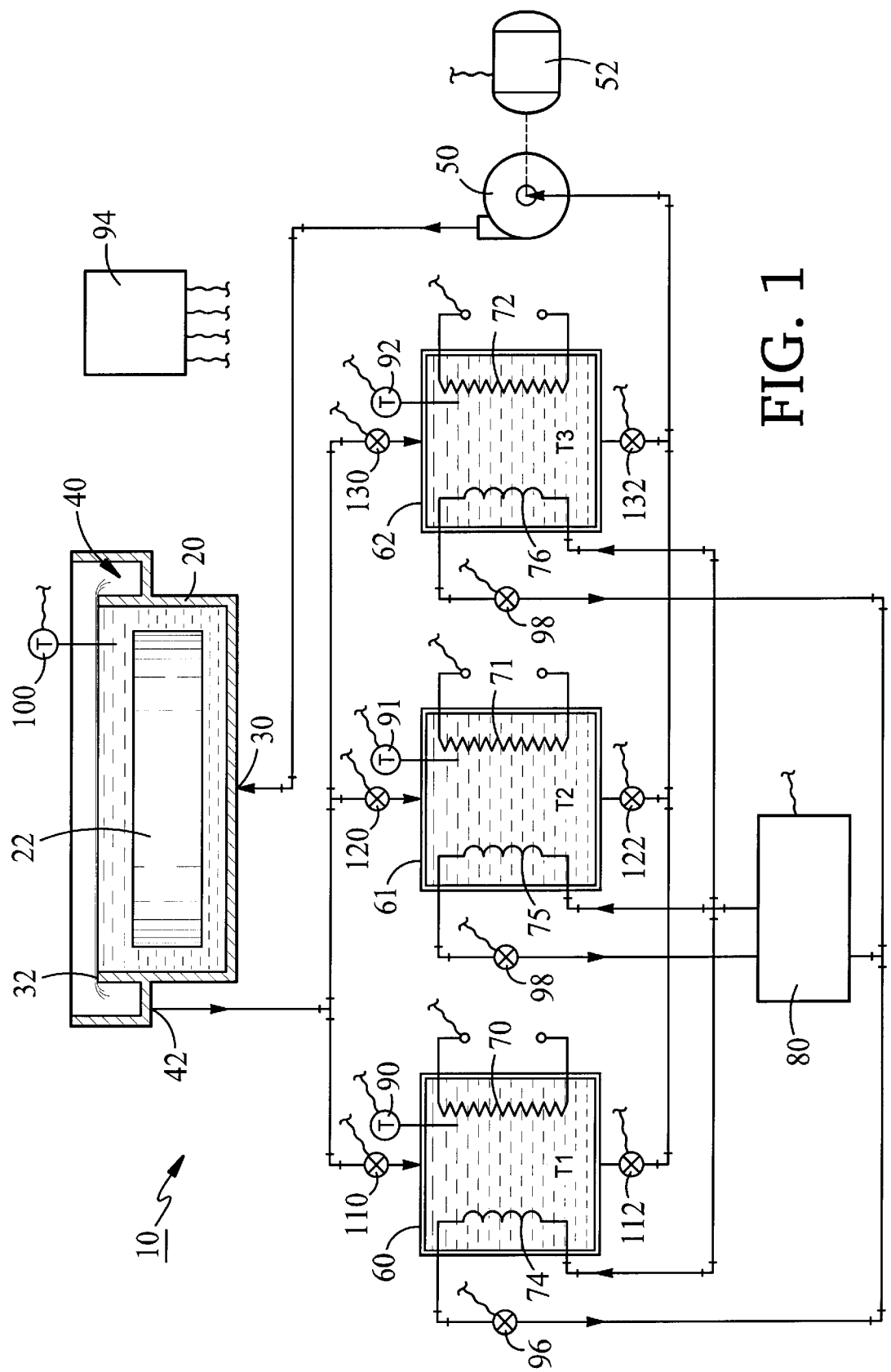
FIG. 1 is schematic representation of a PCR temperature control system according to the present invention.

FIG. 1 illustrates a PCR temperature control system, generally indicated by the reference numeral 10. System 10 includes a thermally insulated tank 20 into which is placed a multiwell sample carrier 22. Tank 20 may be made of a thermally insulating material such as polypropylene. In the case where sample carrier 22 is a roll of carrier tape as described above, the inside of insulated tank 20 would be about 17 inches in diameter and about five inches deep. A water inlet 30 is supplied at the bottom of insulated tank 20 for the introduction of water thereinto, while top 32 of the insulated tank is designed to permit the outlet water to overflow around the perimeter thereof. A gutter 40 defined around and surrounding top 32 collects the overflow and returns it through outlet 42. Circulation of the water is effected by pump 50 and its associated variable speed drive 52.

Separate, vented or open, temperature controlled water tanks 60, 61, and 62 are provided to supply circulating water to insulated tank 20 though pump 50. Tanks 60–62 are held, respectively, at temperatures T-1, T-2, and T-3 by means of electrical heating coils 70–72 and cooling coils 74–76, the latter being supplied with recirculated brine from a chiller unit 80. Temperatures T-1, T-2, and T-3 in tanks 60–62 are sensed, respectively, by temperature sensing elements 90–92 and a master controller 94 connected to receive outputs from the temperature sensing elements closely controls the temperatures by controlling electrical heating coils 70–72 and brine control valves 96–98 connected in the lines from cooling coils 74–76. The temperature in insulated tank 20 is similarly sensed by temperature sensing element 100 and the output thereof passed to master controller 94.

Water from water tank 60 is circulated by pump 50 through insulated tank 20 and returned thereto by means of master controller 94 opening valves 110 and 112. Similarly, water from water tank 61 is circulated by pump 50 through insulated tank 20 and returned thereto by means of master controller 94 opening valves 120 and 122 and from and to water tank 62 by means of the master controller opening valves 130 and 132. Of course, the respective valves on those of tanks 60–62 from which water is not being recirculated will be closed.

In operation, valves 110 and 112 are opened by master controller 94 and water at temperature T-1 from water tank 60 is recirculated through insulated tank 20. When the temperature in insulated tank 20 stabilizes at T-1, pump 50 stops and valve 112 is closed. When the protocol calls for temperature T-2 in insulated tank 20, pump 50 is started and valve 122 on water tank 61 is opened, permitting water from tank 61 to be pumped to the insulated tank. Water at temperature T-1 continues to exit insulated tank 20 and return to water tank 60. When water from insulated tank 20 at temperature T-2 begins to exit that tank, valve 110 is closed, valve 120 is opened, and the water returns to water tank 61. When the temperature in insulated tank 20 stabilizes at T-2, valve 122 is closed and pump 50 is stopped. In a similar manner, water at temperature T-3 is supplied from water tank 62. The sequence is used in such manner as to match the temperature cycles and times called for by the protocol.

Some PCR protocols require controlling the ramp time from one temperature to the next. This is accomplished by the present invention by varying the speed of pump 50 through master controller 94 controlling variable speed drive 52. Pump 50 and its top speed are matched to the fastest rise time required by the desired protocols. Variable speed drive 52 on pump 50 permits the pump to be set to match the slowest ramp time.

Water tanks 60–62 are sized to provide a storage capacity in excess of the volume of insulated tank 20. Typically, each of water tanks 60–62 is about three times the size of insulated tank 20. In addition, electrical coils 70–72 and cooling coils 74–76 are sized to have a fast response time and to quickly control the temperature in their respective water tanks. This excess capacity and fast response time are designed to assure that the desired temperatures are maintained in water tanks 60–62 and then delivered to insulated tank 20.

While three water tanks have been illustrated, it will be understood that the present invention may employ only two water tanks or it may employ a number greater than three water tanks, depending on the protocol being used.

In the embodiments of the present invention described above, it will be recognized that individual elements and/or features thereof are not necessarily limited to a particular embodiment but, where applicable, are interchangeable and can be used in any selected embodiment even though such may not be specifically shown.

Terms such as "upper", "lower", "inner", "outer", "inwardly", "outwardly", and the like, when used herein, refer to the positions of the respective elements shown on the accompanying drawing figures and the present invention is not necessarily limited to such positions.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

I claim:

1. In combination, a polymerase chain reaction temperature control system and a multiwell sample carrier comprising:
    (a) a sample carrier comprising a coil of carrier tape having wells containing therein polymerase chain reaction materials,
    (b) a first tank in which is entirely submerged said sample carrier
    (c) means to introduce first temperature controlled heat transfer medium into said first tank for a first predetermined length of time; and
    (d) means to subsequently introduce at least a second temperature controlled heat transfer medium into said first tank for at least a second predetermined length of time.

2. A polymerase chain reaction temperature control system, as defined in claim 1, wherein: said first temperature controlled heat transfer medium and said at least said second temperature controlled heat transfer medium are recirculated, respectively, from first and at least second temperature controlled supply tanks.

3. A polymerase chain reaction temperature control system, as defined in claim 2, wherein: said first and at least second temperature controlled supply tanks have associated therewith heating and cooling means that provide response around selected temperature control points.

4. A polymerase chain reaction temperature control system, as defined in claim 1, wherein: said first temperature controlled heat transfer medium is introduced into said first tank and recirculated therethrough by means of a pump.

5. A polymerase chain reaction temperature control system, as defined in claim 4, wherein: a controller controls rate of pumping of said pump to control ramp time of temperature change of said sample carrier.

6. A method of conducting a polymerase chain reaction comprising:
    (a) providing a first tank in which is entirely submerged a sample carrier comprising a coil of carrier tape having wells containing therein polymerase chain reaction materials;
    (b) introducing a first temperature controlled heat transfer medium into said first tank for a first predetermined length of time; and
    (c) subsequently introducing at least a second temperature controlled heat transfer medium into said first tank for at least a second predetermined length of time.

7. A method of conducting a polymerase chain reaction, as defined in claim 6, further comprising: recirculating said first temperature controlled heat transfer medium and said at least said second temperature controlled heat transfer medium, respectively, from first and at least second temperature controlled supply tanks.

8. A method of conducting a polymerase chain reaction, as defined in claim 7, further comprising: providing said first and at least second temperature controlled supply tanks with heating and cooling means that provide response around selected temperature control points.

9. A method of conducting a polymerase chain reaction, as defined in claim 6, further comprising: introducing said first temperature controlled heat transfer medium into said first tank and recirculating said first temperature controlled heat transfer medium therethrough by means of a pump.

10. A method of conducting a polymerase chain reaction, as defined in claim 9, further comprising: providing a controller to control rate of pumping of said pump to control ramp time of temperature change of said sample carrier.

* * * * *